US012755360B2

(12) United States Patent
Rohleder et al.

(10) Patent No.: US 12,755,360 B2
(45) Date of Patent: Oct. 6, 2026

(54) METHOD FOR MONITORING A SURGICAL INTERVENTION WITH X-RAY IMAGING, AND MEDICAL X-RAY SYSTEM

(71) Applicant: Siemens Healthineers AG, Forchheim (DE)

(72) Inventors: Maximilian Rohleder, Erlangen (DE); Björn Kreher, Bräuningshof (DE); Holger Kunze, Bubenreuth (DE); Gerhard Kleinszig, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 133 days.

(21) Appl. No.: 18/824,393

(22) Filed: Sep. 4, 2024

(65) Prior Publication Data

US 2025/0086766 A1 Mar. 13, 2025

(30) Foreign Application Priority Data

Sep. 13, 2023 (DE) ..................... 10 2023 208 900.9

(51) Int. Cl.
*G06T 7/00* (2017.01)
*A61B 90/00* (2016.01)

(52) U.S. Cl.
CPC .......... *G06T 7/00* (2013.01); *A61B 2090/376* (2016.02); *G06T 2207/10116* (2013.01)

(58) Field of Classification Search
CPC ........................................................ G06T 7/00
See application file for complete search history.

(56) References Cited

U.S. PATENT DOCUMENTS

2016/0171714 A1 6/2016 Ekin
2020/0126229 A1* 4/2020 Lavi ...................... G06T 7/0014
2024/0005551 A1* 1/2024 Blau ......................... G06T 7/60
2024/0099775 A1* 3/2024 Blau ...................... A61B 34/10

FOREIGN PATENT DOCUMENTS

WO 2013136239 A1 9/2013

OTHER PUBLICATIONS

Wikipedia, "Epipolar Geometry" obtained Aug. 22, 2024. pp. 1-2. https://en.wikipedia.org/wiki/Epipolar_geometry.

* cited by examiner

*Primary Examiner* — Edward Park
(74) *Attorney, Agent, or Firm* — Lempia Summerfield Katz LLC

(57) ABSTRACT

A method for monitoring a surgical intervention with X-ray imaging by way of a recording system that is adjustable into different angulations includes recording a first projection image of an implant in a first angulation and, following a forward movement of the implant, recording a third projection image of the implant in a third angulation. The method further includes establishing the original position of the tip of the implant in the first projection image, establishing the advanced position of the tip of the implant in the third projection image, establishing a first epipolar line for the advanced position of the tip in the first projection image by the epipolar geometry determined by way of the first and the third angulation, and simultaneously displaying the first and the third projection images, wherein the established epipolar line is shown in the first projection image.

17 Claims, 5 Drawing Sheets

METHOD FOR MONITORING A SURGICAL INTERVENTION WITH X-RAY IMAGING, AND MEDICAL X-RAY SYSTEM

The present patent document claims the benefit of German Patent Application No. 10 2023 208 900.9, filed Sep. 13, 2023, which is hereby incorporated by reference in its entirety.

TECHNICAL FIELD

The disclosure relates to a method for monitoring a surgical intervention with X-ray imaging and a medical X-ray system for carrying out a method of this type.

BACKGROUND

In orthopedic surgery and trauma surgery, screws, wires, and other implants are introduced into bones. This represents a great challenge because the respective implant must be positioned very precisely, dependent upon the patient anatomy and the intervention to be carried out, in narrow channels in order to prevent damage to surrounding tissues and to provide a successful performance of the intervention. A high quality imaging for monitoring the intervention is therefore indispensable during the introduction of the implant.

Two different approaches exist for this, each of which may be selected dependent upon the complexity of the intervention. In certain cases, a large number of two-dimensional (2D) projection images are prepared in at least two different angulations, wherein changing between the angulations may take place in order to obtain a three-dimensional understanding of the implantation procedure relative to the patient anatomy. In particularly complex cases, surgical navigation systems are used in combination with three-dimensional (3D) cone beam computed tomography (CBCT) imaging and external tracking in order to monitor the introduction of screws. In this case, an external camera system measures the relative position between the patient anatomy and the implant by markers that are fastened to both.

SUMMARY AND DESCRIPTION

It is an object to provide a method that, in certain cases of surgical interventions, simplifies the monitoring of the introduction of implants, for example, into bones. It is a further object to provide a medical X-ray system suitable for carrying out the method.

The object is achieved with a method for monitoring a surgical intervention with X-ray imaging and with a medical X-ray system as described herein. The scope of the present disclosure is defined solely by the appended claims and is not affected to any degree by the statements within this summary. The present embodiments may obviate one or more of the drawbacks or limitations in the related art.

A method is provided for monitoring a surgical intervention with X-ray imaging by way of a recording system that is adjustable into different angulations, having an X-ray source and an X-ray detector, during which intervention into (or on) the anatomy of an examination object, an implant having a tip is moved forward along a movement axis with the tip foremost. The method includes: recording a first projection image of the implant in a first angulation; recording of a third projection image of the implant in a third angulation following a forward movement of the implant; optionally establishing the original position of the tip of the implant in the first projection image; establishing the advanced position of the tip of the implant in the third projection image; establishing a first epipolar line for the advanced position of the tip in the first projection image by the epipolar geometry determined by way of the first and the third angulation; and simultaneously displaying the first and the third projection images, wherein the established epipolar line is shown in the first projection image.

By way of the method, the user may visualize the updated advanced position of the tip of the implant in at least one additional projection image of a further angulation particularly rapidly and easily without additional displacement of the recording system and, if needed may also visualize it with a large number of projection images of many angulations. The user does not need to record an updated projection image for each angulation, but rather may use the epipolar lines in order to update and display the advanced position of the tip. With the aid of the updated third projection image, in the original first projection image that was recorded before the movement, the updated advanced position may be visualized.

By way of the method, the X-ray dose may be reduced and also the expenditure of much time and effort in the adjustment of the recording system may be spared. At the same time, a good and precise monitoring of an intervention with a forward-moving implant is possible. Overall, the radiation burden and therefore the risk to the health of the patient is reduced and the treatment success is maximized. The method enables, for the user, a more intuitive understanding of the three-dimensional surgical scene. In addition, the simultaneous visualization of at least two and/or even a large number of projection directions helps the user (for example, a surgeon) to assess the situation more reliably. In particular, previously unused geometrical information may be used. The method enables effectively three-dimensional views without having to carry out an actual 3D imaging.

In the following, the tip of the implant should be understood to be the point of the implant arranged furthest forward in the movement direction, wherein it is not necessarily an implant narrowing to a point. What is important is that for the establishment of the epipolar lines, a “point” is used, that is, not a shape extending significantly in different directions.

An angulation should be understood to be the projection geometry of the recording system, that is, the position of the X-ray source and the X-ray detector and the projection angle of the X-ray beam (central ray) in relation to the examination object.

It should be noted that the first angulation differs from the third angulation since otherwise an epipolar geometry is not possible.

According to one embodiment, the method further includes: recording a second projection image of the implant in a second angulation different from the first angulation before the forward movement, establishing the original position of the tip of the implant in the second projection image, establishing from a second epipolar line for the advanced position of the tip in the second projection image by the epipolar geometry determined by way of the second and the third angulation, and display of the second projection image simultaneously with the first and the third projection images, wherein the established second epipolar line is shown in the second projection image. Overall herein, three angulations are used in order for the user to receive an even better overview of the intervention. By way of the different angulations, in particular, as far as possible from one another, the user receives an effectively three-dimensional impression of the intervention. Sites that are difficult to pass for the forward movement of the implant may be overseen and evaluated from different directions. For this purpose, before the movement of the implant, just two projection images need to be recorded with different angulations.

According to a further embodiment, the (projected) movement axis of the forward movement of the tip of the implant is displayed (for example, superimposed) in the first and/or the second projection image. In this way, the user may discern at a glance what the effect of the forward movement of the implant in the projection plane is likely to be. In particular, the movement axis is determined as an extrapolation of a longitudinal axis of the implant on the basis of the first and/or second projection image and is displayed in the first and/or second projection image. Thus, for example, the implant may be identified by segmentation and/or image recognition and therefrom a longitudinal axis of the implant may be determined. This may be implemented particularly simply and rapidly.

According to a further embodiment, the respective intersection point of the epipolar line with the movement axis (for example, extrapolated longitudinal axis) is determined and displayed. In this way, the current advanced position of the tip may be displayed, very simply and easily recognizably, in the first and second projection image. This represents a rapid and precise visualization of the current advanced position on a plurality of (and/or as many as desired) projection images, wherein in fact only a single current projection image is needed.

According to one embodiment, for the establishment of the original position and/or of the advanced position and/or of the implant in the projection images, a segmentation and/or an image recognition is carried out. Known software algorithms may be used for this purpose.

Advantageously, for a three-dimensional impression of the forward movement of the implant, the third angulation differs from the first and the second angulation.

According to one embodiment, the first, second, and third projection images are displayed beside one another and/or below one another. This may be arranged as needed by the user in order to receive an optimum overview of the intervention. A plurality of display units (for example, monitors, touchscreens, etc.) may also be used.

According to a further embodiment, the movement axis is superimposed on the projection images and/or drawn in and/or marked or otherwise optically displayed. If needed, this may also be carried out in color.

According to a further embodiment, at least one further projection image is recorded in the third angulation, a further advanced position of the tip of the implant is established on each further projection image, further epipolar lines are established in the first and the second projection image from the epipolar geometry that is determined by way of the first and third and/or second and third angulation with the advanced position of the tip, and the further epipolar lines established are displayed in the first and second projection image. In this way, any desired number of advanced positions of the tip of the implant may be visualized and the entire intervention may be optimally monitored.

The disclosure further includes a medical X-ray system for carrying out the method described above, having an X-ray imaging device with a recording system that is adjustable into different angulations, having an X-ray source and an X-ray detector for recording X-ray images, a system control unit for controlling the medical X-ray system, an imaging system for analyzing the X-ray images, in particular, for image recognition, an evaluating unit for establishing epipolar lines, and a display unit for displaying the X-ray images and epipolar lines. In an advantageous manner, the X-ray system has at least one movement sensor and/or angle sensor and/or encoder for measuring the adjustment of the movement or rotation axes. In particular, a plurality of or all the movement and rotation axes of the X-ray system are equipped with movement and angle sensors and/or encoders in order therefrom to be able to derive the extrinsics of the projection geometry.

BRIEF DESCRIPTION OF THE DRAWINGS

The disclosure and further advantageous embodiments are now described in greater detail on the basis of exemplary embodiments illustrated schematically in the drawings, but without any restriction of the disclosure to these exemplary embodiments arising therefrom. In the drawings.

DETAILED DESCRIPTION

Figure 1:
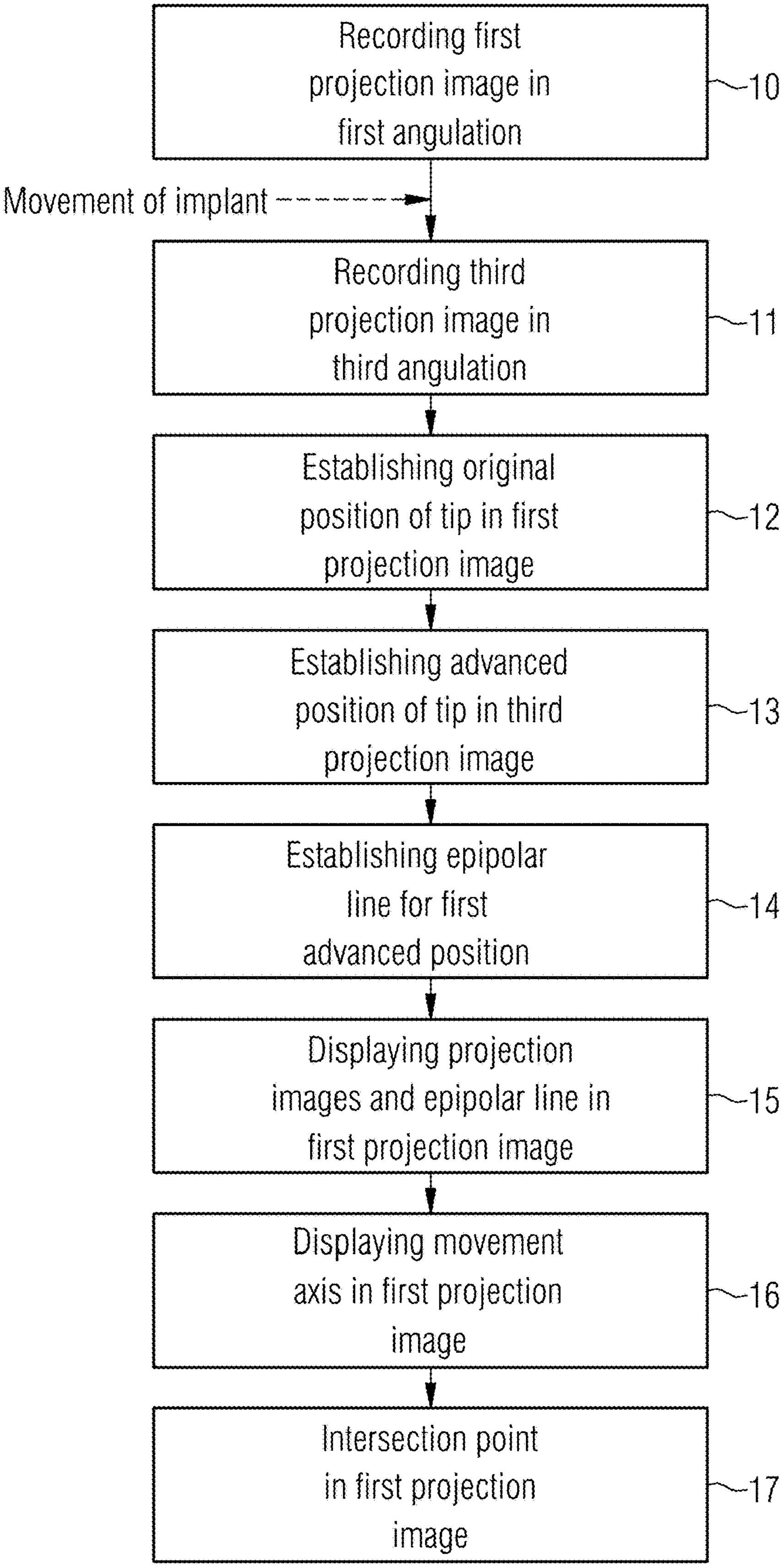
FIG. 1 depicts an example of a sequence of acts of a method for monitoring a surgical intervention with X-ray imaging.
Figure 2:
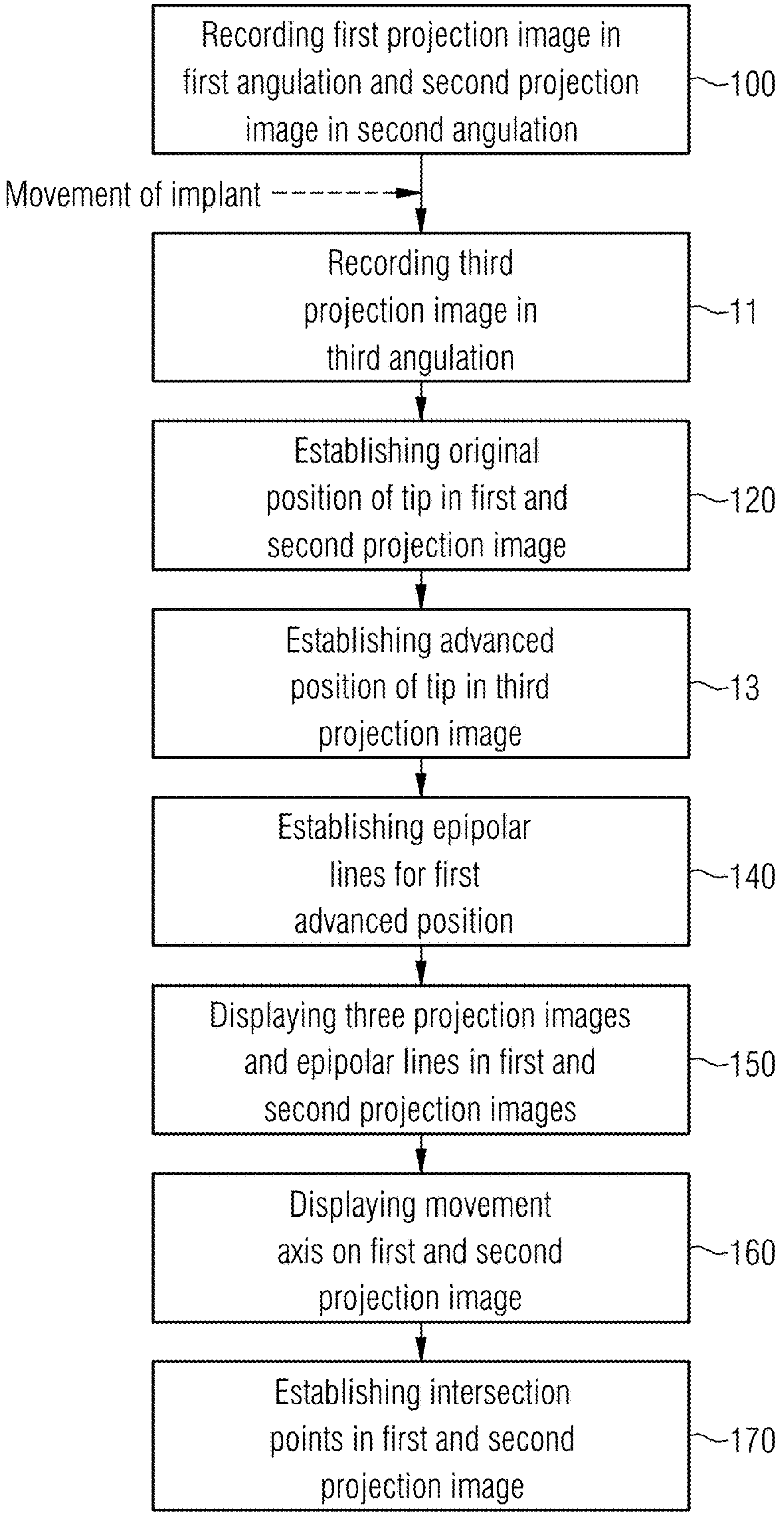
FIG. 2 depicts a further example of a sequence of acts of a method for monitoring a surgical intervention with X-ray imaging.

In FIGS. 1 and 2, two embodiments of the method for monitoring a surgical intervention with X-ray imaging by way of a recording system adjustable into different angulations are shown.

The method is used, for example, for monitoring an intervention on a patient in orthopedic surgery in which, for example, screws, wires, or other implants are introduced into tissue and/or bone. By way of the monitoring method, it is possible to keep a comprehensive overview of the movement progress of the implant with a simultaneously low X-ray burden. Following initial recording from at least two different angulations, the user needs only to record further projection images from one projection direction and thereby may see the progress of the implant from two or more projection directions. By this, it is possible to position the implant very precisely and, in the context of the intervention, to avoid damage to surrounding tissues of the patient.

The monitoring takes place by way of X-ray imaging by way of a recording system (for example, in the form of a C-arm) of an X-ray system that is adjustable into different angulations (e.g., projection directions), wherein the C-arm has an X-ray source and an X-ray detector. During the intervention, an implant that has a front point and/or a tip, is moved forward in a straight line in the anatomy of an examination object along a movement axis with the tip in front. Most implants are elongated and thereby have a clear longitudinal axis, (e.g., implants such as screws, catheters, guide wires, or nails). In certain cases, (e.g., in orthopedic surgery), it may be assumed that the longitudinal axis corresponds to the movement axis/advancing axis. This may be exploited in the present case. Alternatively, a movement axis may be established, calculated, or estimated by other methods, devices, or systems.

Figure 6:
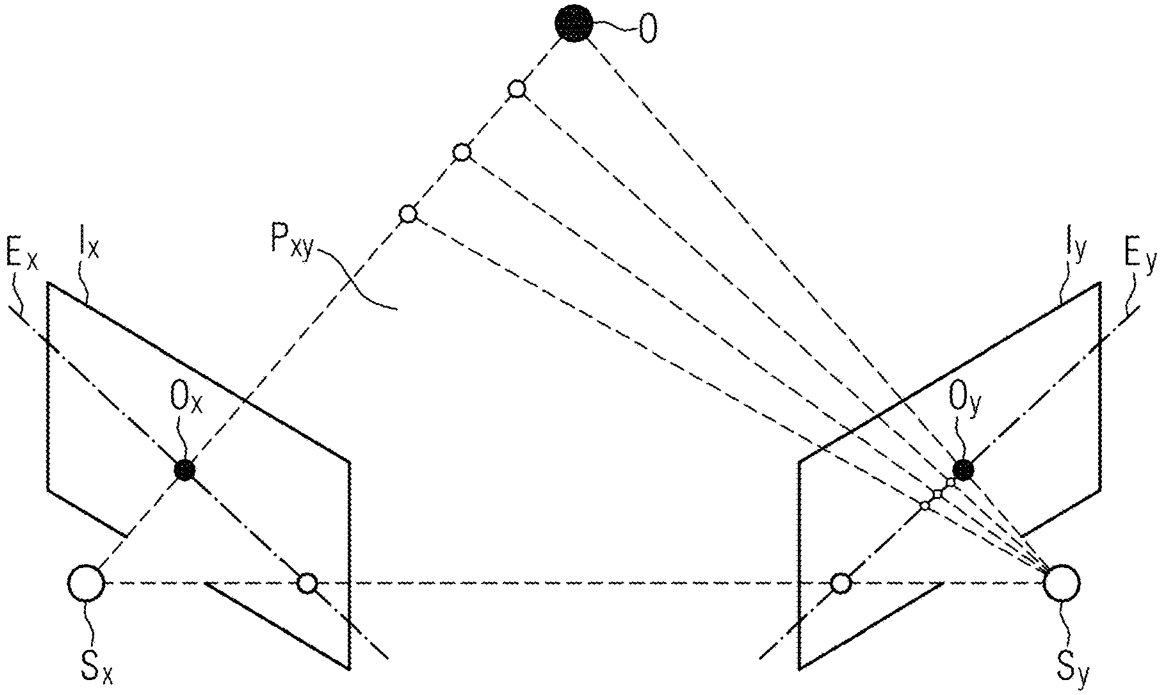
FIG. 6 depicts a known view of the epipolar geometry during the recording of images of an object from two projection directions.

In FIG. 6, known geometric relationships and the functional principle in the determination of epipolar lines are shown on the basis of epipolar geometry: from two different projection directions, from an xth projection center $S_x$, an xth image $I_x$, and from an yth projection center $S_y$, an yth image $I_y$ of a punctiform object O, and its surroundings are recorded (for example, with a camera). In the images $I_x$ and $I_y$, the object O is mapped as the xth object projection Ox and the yth object projection Oy. The x-y epipolar plane $E_{xy}$ is generated by the xth projection center $S_x$ and the yth projection center $S_y$ and the actual 3D position of the object O. The line of intersection of the x-y epipolar plane $E_{xy}$ with the xth image $I_x$ forms the xth epipolar line Ex and with the yth image $I_y$, it forms the yth epipolar line $E_y$. Geometrical relationships of this type are, in principle, known from the prior art, for example, https://de.wikipedia.org/wiki/Epipolargeometrie.

The disclosure makes use of the fact that in X-ray imaging, with arbitrary angulations of a recording system (such as a C-arm), the spatial projection geometry is known and/or, for example, may be determined with the aid of sensors/encoders on the axes. In addition, the fact is utilized that with a straight-line forward movement of a point, which is for example, the tip of the implant, its movement axis is determined or estimated and may be drawn into a projection image.

Figure 3:
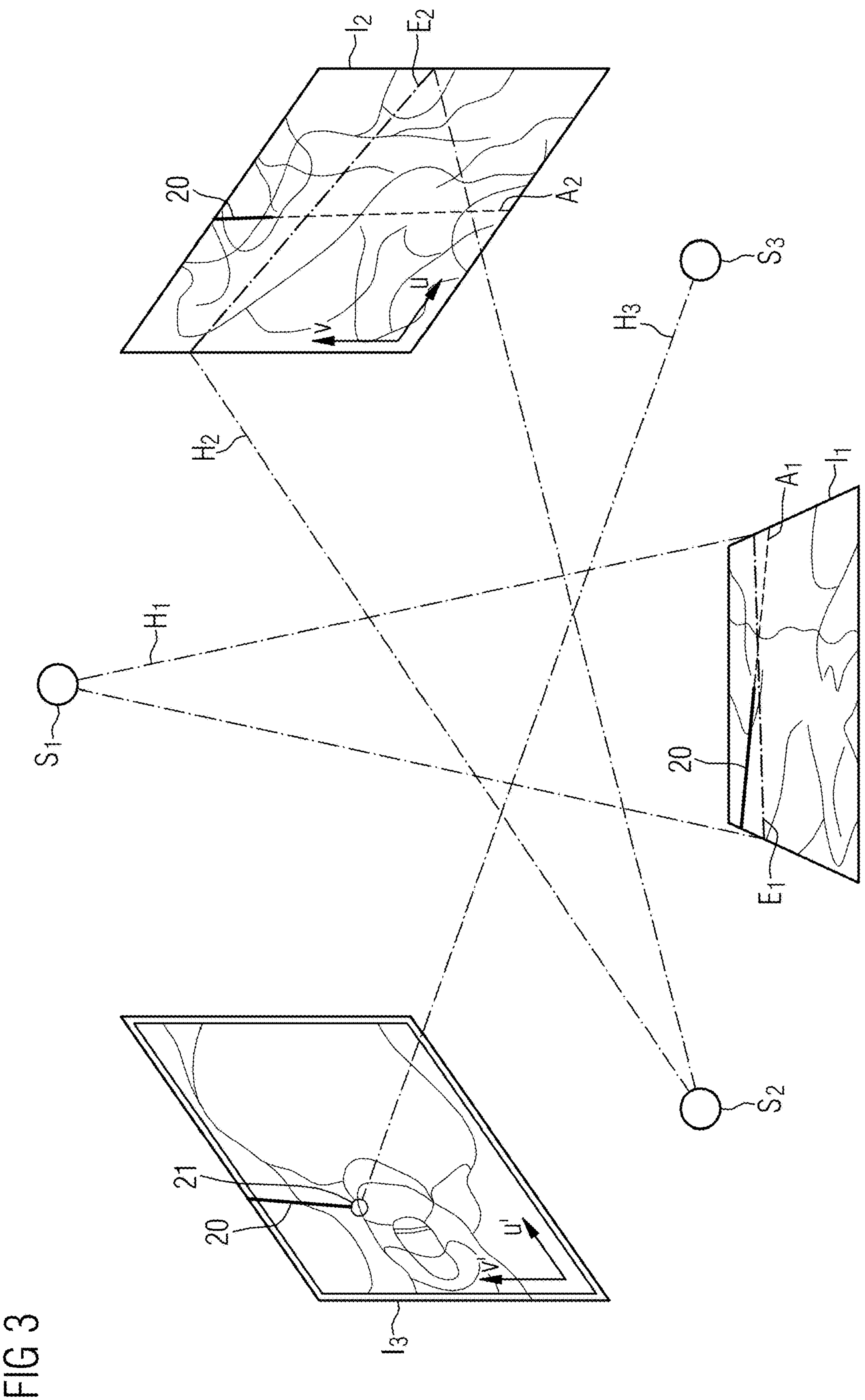
FIG. 3 depicts a view of the epipolar geometry during the recording of three projection images according to the method.

In act 10 (FIG. 1), a first projection image $I_1$ of the implant arranged in the examination object (for example, the body of a patient) is recorded in a first angulation (see, e.g., in FIG. 3, the three-dimensional spatial relationships, wherein the first projection center Si corresponds, for example, to the position of the focus point of the X-ray source 31 at the first angulation and the projection image $I_1$ corresponds to the position of the X-ray detector at the first angulation). The recording of the first projection image may be carried out, for example, before the start of the forward movement of the implant that is to be monitored. Thus, for example, during an intervention in which an implant (for example a screw) is to be introduced into the bone, the implant may be positioned in advance on the cortical bone as the starting position for traversing the bone and the movement axis may have been fixed (not part of the method). The recording system (C-arm) may be aligned for the recording of the first projection image on the basis of the desired movement axis of the implant.

In the first projection image $I_1$, in particular, the implant 20 and the tip 21 of the implant are imaged, wherein the position of the tip 21 is designated the original position.

Following completion of a forward movement of the implant and its tip, in act 11, a third projection image $I_3$ of the implant is recorded in a third angulation of the recording system that differs from the first angulation. In the third projection image $I_3$ also, the implant 20 and the tip 21 of the implant are mapped, wherein the tip 21 has an advanced position (that is, after the forward movement has taken place). In FIG. 3, the three-dimensional spatial relationships are shown, wherein the third projection center $S_3$ corresponds to the position of the focus point of the X-ray source 31 at the third angulation and the projection image $I_3$ corresponds to the position of the X-ray detector at the third angulation.

In optional act 12, the original position of the tip of the implant in the first projection image $I_1$ is established, for example, by way of a segmentation and/or image recognition software that is operated on an imaging system. Such image recognition methods are sufficiently well known. Furthermore, the implant (if mapped) may also be completely recognized, for example, in order to be able to determine and/or estimate its longitudinal axis. Act 12 may also be carried out at another time point, for example, directly after the recording. In act 13, the advanced position of the tip of the implant (optionally also the implant) is established in the third projection image $I_3$. This may also be carried out in the imaging system by way of known segmentation and/or image recognition software.

In act 14, using the known projection geometry of the first and the third angulation (as shown in FIG. 3), a first epipolar line $E_1$ is determined in the first projection image $I_1$, which first epipolar line $E_1$ represents the projection, established from the third projection image, of the advanced position of the tip in the first projection image $I_1$. The first epipolar line $E_1$ comes into existence by way of the projection of the spatially arranged connecting line $H_3$ between the third projection center $S_3$ and the advanced position of the tip of the implant onto the first projection image $I_1$.

In act 15, the first projection image $I_1$ and the third projection image $I_3$ are displayed, for example, on a display unit or a display, for example, as a split-screen, wherein the first epipolar line $E_1$ is mapped in the first projection image $I_1$, for example, superimposed, overlaid, drawn in, etc. The projection images may be shown, for example, beside one another and/or above one another. The display takes place such that the user receives a particularly good overview of the intervention. Shown in FIG. 4 is an example of a display of this type, wherein apart from the first projection image $I_1$ and the third projection image $I_3$, a second projection image $I_2$ (to be addressed below) is also shown.

Figure 4:
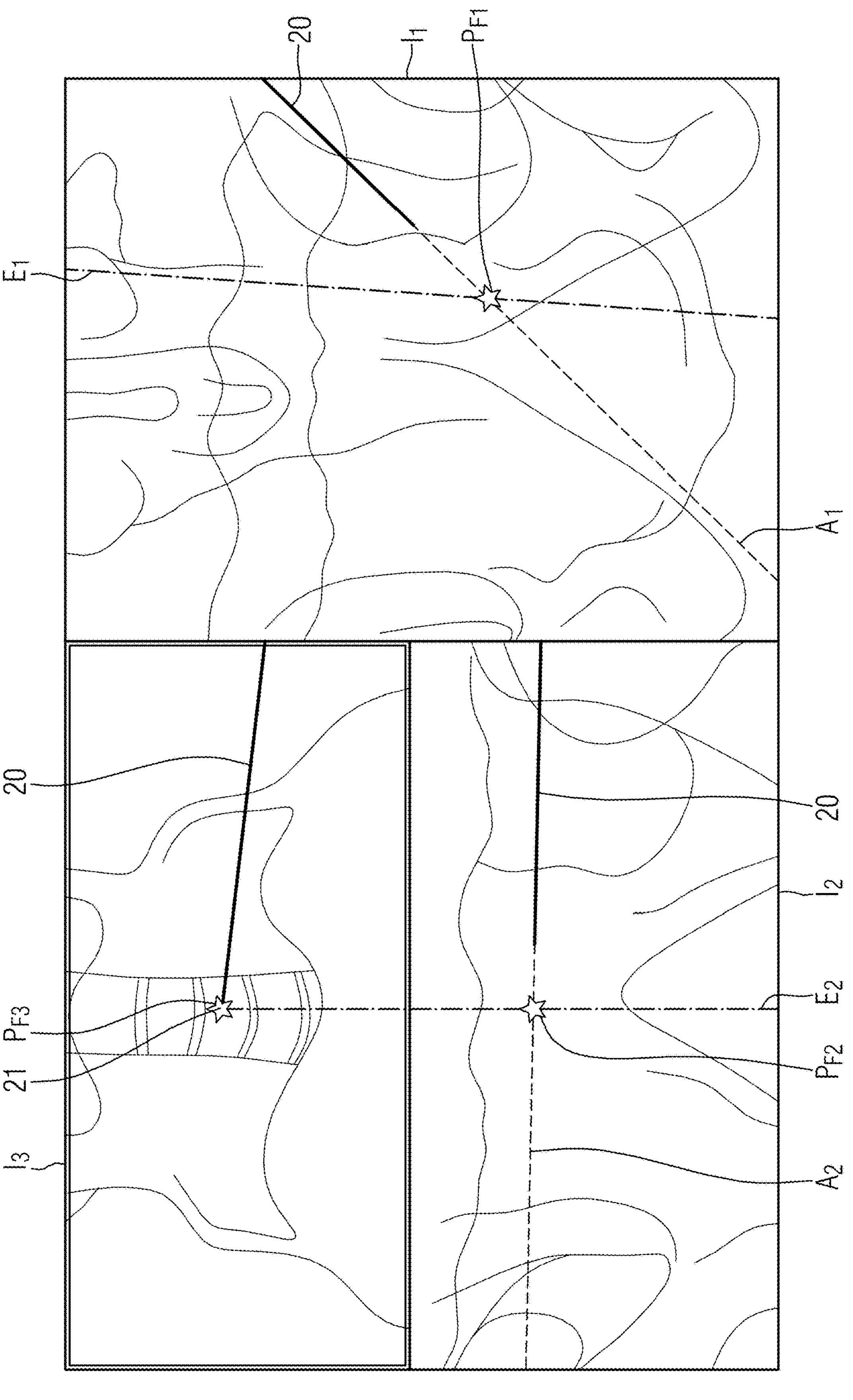
FIG. 4 depicts an example of the representation of three projection images with epipolar lines according to the method.

In act 16, the predicted movement axis $A_1$ of the tip of the implant is shown in the first projection image $I_1$, for example, superimposed, overlaid, or drawn in (see FIG. 3 and FIG. 4). For this purpose, the movement axis $A_1$ is established in advance, (e.g., calculated or estimated). The movement axis $A_1$ of the tip of the implant in the first projection image $I_1$ may be determined, for example, as an extension or extrapolation of the longitudinal axis of the implant 20 (and/or its projection onto the first projection image $I_1$). Then, in act 17, from the intersection point of the movement axis $A_1$ and the first epipolar line $E_1$ in the first projection image $I_1$, the advanced position $P_{F1}$ of the tip of the implant in the first projection image $I_1$ is found.

In FIG. 2, a further method is shown, wherein in this example, in place of the act 10, in act 100 before the forward movement of the implant, a first projection image $I_1$ in a first angulation and a second projection image $I_2$ in a second angulation are recorded, wherein the two angulations differ. In particular, significantly different angulations may be used in order to obtain the most comprehensive overview. In further embodiments (not shown), a plurality of projection images with many different angulations may also be recorded, depending upon how many views the user wishes to have. Act 11 in FIG. 2 corresponds to the method in FIG. 1.

In place of act 12, optionally, in act 120, the original position of the tip of the implant in the first projection image $I_1$ and in the second projection image $I_2$ is established (alternatively also in further projection images), again, for example, by way of segmentation or image recognition software. Act 13 in FIG. 2 corresponds to the method in FIG. 1.

In place of act 14, subsequently in act 140, using the known projection geometry of the first and the third angulation, a first epipolar line $E_1$ is determined in the first projection image $I_1$, which first epipolar line $E_1$ represents the projection, established from the third projection image, of the advanced position of the tip in the first projection image $I_1$. Additionally, making use of the known projection geometry of the second and the third angulation, a second epipolar line $E_2$ in the second projection image $I_2$ is determined, which second epipolar line $E_2$ represents the projection, established from the third projection image, of the advanced position of the tip in the second projection image $I_2$. The first epipolar line $E_1$ comes into existence by way of the projection of the spatial connecting line $H_3$ between the third projection center $S_3$ and the advanced position of the tip of the implant onto the first projection image $I_1$ and the second epipolar line $E_2$ comes into existence by way of the projection of the spatial connecting line $H_3$ between the third projection center $S_3$ and the advanced position of the tip of the implant in the second projection image $I_2$.

Alternatively, further epipolar lines may also be determined in further projection images.

In place of act 15, subsequently, in act 150, the first projection image $I_1$, the second projection image $I_2$ and the third projection image $I_3$ are displayed, for example, on a display unit or a display, wherein the first epipolar line $E_1$ is mapped in the first projection image $I_1$ and the second epipolar line $E_2$ is mapped in the second projection image $I_2$, for example, superimposed, overlaid, drawn in, etc. (see FIG. 3). The projection images may be shown for example beside one another and/or above one another (see FIG. 4). If required, many projection images may also be displayed.

In place of act 16, in act 160, the movement axis $A_1$ of the tip of the implant is displayed in the first projection image $I_1$ and the movement axis $A_2$ of the tip of the implant in the second projection image $I_2$ is displayed, for example, superimposed, overlaid, or drawn in (see FIG. 3 and FIG. 4). For this purpose, the movement axes $A_1$ and $A_2$ are established in advance, for example, calculated or estimated. The movement axes may be determined, for example, as extensions or extrapolations of the longitudinal axis of the implant 20 (and/or as a corresponding projection).

In act 170, from the intersection point of the movement axis $A_1$ and the first epipolar line $E_1$ in the first projection image $I_1$, the advanced position $P_{F1}$ of the tip of the implant in the first projection image $I_1$ is found and, from the intersection point of the movement axis $A_2$ and the second epipolar line $E_a$ in the second projection image $I_2$, the advanced position $P_{F2}$ of the tip of the implant in the second projection image $I_2$ is found (see FIG. 4).

Overall, the sequence of the acts may also be varied.

In order to visualize further forward movements of the implant during the intervention, the method and/or the recording of respectively updated projection images with further updated advanced positions of the tip and corresponding determinations and representations of epipolar lines may be repeated as often as desired. In this way, the entire intervention and/or the entire forward movement may be visualized by increments. On the display, each updated projection image may then be displayed together with the projection images recorded before the forward movement and in the latter, the respective current advanced position may be displayed with the current epipolar lines. The movement axes may be retained, so that again the further updated advanced positions are determined by way of the intersection points.

The superimposition of the epipolar lines and the movement axes offer to the user valuable additional information that comes close to a three-dimensional representation. In this way, the progress of the implant, for example, into bone or tissue may be observed constantly. Since the direction of the movement axis does not change, the updated advanced position of the tip may be visualized in a large number of projection images and enables a more intuitive understanding of the three-dimensional surgical scene.

The method saves time and patient dose, since the old projection images from other angulations do not have to be renewed, but nevertheless may display the current advanced position of the tip of the implant. In addition, the simultaneous visualization of a large number of projection directions helps the user to assess the situation precisely and reliably. In particular, the proposed superimposition uses previously unused geometrical information. The main difference of the method from navigation-based solutions includes the independence of 3D imaging and of external tracking systems. The method is simple, economical, requires less hardware, saves time, and saves X-ray dose.

Figure 5:
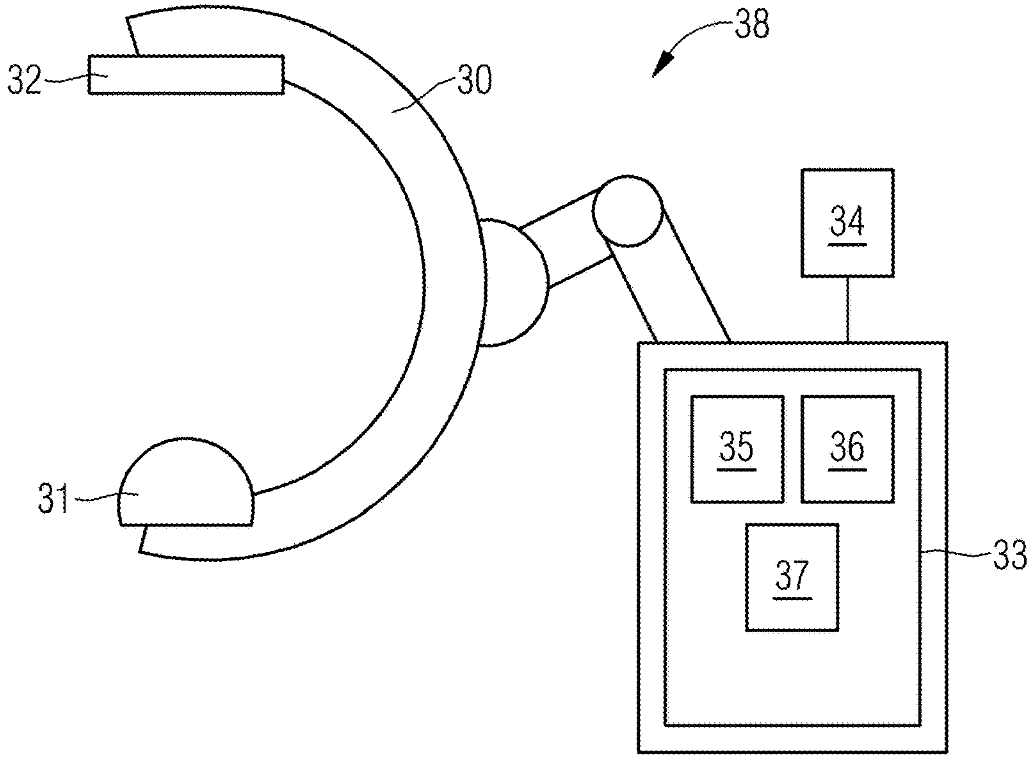
FIG. 5 depicts an example of a medical X-ray system for carrying out the method.

FIG. 5 shows a medical X-ray system 38 for carrying out the method described. The medical X-ray system 38 has, for example, a recording system in the form of a C-arm 30 with an X-ray source 31 and an X-ray detector 32, which C-arm 30 is able to be placed into a large number of angulations. The medical X-ray system 38 is controlled by a system controller 33, for example, to carry out the method and to record projection images. In addition, the medical X-ray system 38 has an imaging system 35 configured for processing projection images, in particular with software for segmentation and/or image recognition. The image system 33 and/or the corresponding software may recognize, for example, objects such as an implant and its tip in the projection images. Furthermore, an evaluating unit 36 for establishing epipolar lines is provided, wherein the relevant information, for example, regarding the angulation, is provided by the system controller. Furthermore, a display unit 34 is provided for display of the X-ray images, the established epipolar lines, and the extrapolated movement axes. The medical X-ray system 38 may also have a storage unit 37.

A medical X-ray system 38 of this type for carrying out the method may be formed, for example, by a mobile C-arm X-ray device. For precise determination of the angulations (position/orientation of X-ray source and X-ray detector) and/or of the entire epipolar geometry, for example, encoder information regarding the movement axes of the recording system may be read out and used. External sensors may also be used for position determination. The method uses such known positions of the C-arm in order to generate the corresponding visualization in the projection images.

The disclosure may be briefly summarized as follows: for reliable monitoring of interventional procedures with longitudinal implants using the lowest possible X-ray dose, a method is provided for monitoring a surgical intervention with X-ray imaging by way of a recording system that is adjustable into different angulations, having an X-ray source and an X-ray detector, during which intervention in the anatomy of an examination object, an implant having a tip is moved forward along a movement axis with the tip foremost, wherein the method includes: recording a first projection image of the implant in a first angulation; following a forward movement of the implant, recording a third projection image of the implant in a third angulation; establishing the original position of the tip of the implant in the first projection image; establishing the advanced position of the tip of the implant in the third projection image; establishing a first epipolar line for the advanced position of the tip in the first projection image by the epipolar geometry determined by way of the first and the third angulation; and simultaneously displaying the first and the third projection images, wherein the established epipolar line is shown in the first projection image.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring a surgical intervention with an X-ray imaging device by way of a recording system of the X-ray imaging device that is adjustable into different angulations, having an X-ray source and an X-ray detector, during which intervention in an anatomy of an examination object, an implant having a tip is moved forward along a movement axis with the tip foremost, the method comprising:

recording a first projection image, by the X-ray imaging device, of the implant in the anatomy of the examination object in a first angulation;

recording a third projection image, by the X-ray imaging device, of the implant in the anatomy of the examination object in a third angulation after a forward movement of the implant along the movement axis;

establishing an advanced position of the tip of the implant in the third projection image;

establishing a first epipolar line for the advanced position of the tip in the first projection image by an epipolar geometry determined by way of the first angulation and the third angulation; and simultaneously displaying the first projection image and the third projection image, wherein the first epipolar line is shown in the first projection image.

2. The method of claim 1, further comprising:

establishing an original position of the tip of the implant in the first projection image.

3. The method of claim 1, further comprising:

recording a second projection image, by the X-ray imaging device, of the implant in a second angulation different from the first angulation, before the forward movement;

establishing an original position of the tip of the implant in the second projection image;

establishing a second epipolar line for the advanced position of the tip in the second projection image by the epipolar geometry determined by way of the second angulation and the third angulation;

displaying the second projection image simultaneously with the first projection image and the third projection image; and displaying the second epipolar line in the second projection image.

4. The method of claim 3, wherein the first projection image, the second projection image, and the third projection image are displayed beside one another or below one another.

5. The method of claim 3, further comprising:

displaying the movement axis of the forward movement of the tip of the implant.

6. The method of claim 5, wherein the movement axis is determined as an extrapolation of a longitudinal axis of the implant and is displayed in the first projection image and/or the second projection image.

7. The method of claim 6, further comprising:

determining and displaying the respective intersection point of the respective epipolar line with the movement axis.

8. The method of claim 3, further comprising:

carrying out an image recognition for the establishing of the original position and/or the advanced position of the tip of the implant in the first projection image, the second projection image, and/or the third projection image.

9. The method of claim 3, wherein the third angulation differs from the first angulation and the second angulation.

10. The method of claim 3, wherein the third angulation is equal to the first angulation or the second angulation.

11. The method of claim 3, further comprising:

recording at least one further projection image in the third angulation;

establishing a further advanced position of the tip of the implant in each further projection image of the at least one further projection image;

establishing further epipolar lines in the first projection image and the second projection image from the epipolar geometry determined by way of the first angulation and the third angulation and/or the second angulation and the third angulation with the advanced position of the tip; and displaying the further epipolar lines in the first projection image and the second projection image.

12. The method of claim 1, further comprising:

carrying out an image recognition for an establishing of an original position of the tip of the implant in the first projection image and/or for the establishing of the advanced position of the tip of the implant in the third projection image.

13. The method of claim 1, wherein the third angulation differs from the first angulation.

14. The method of claim 1, wherein the third angulation is equal to the first angulation.

15. The method of claim 1, wherein the first projection image and/or the third projection image are displayed beside one another or below one another.

16. The method of claim 1, wherein the movement axis is superimposed onto the first projection image and the third projection image, drawn in, marked, or a combination thereof.

17. A medical X-ray system comprising:

an X-ray imaging device with a recording system adjustable into different angulations, having an X-ray source and an X-ray detector, wherein the X-ray imaging device is configured to record a first projection image of an implant in an anatomy of an examination object in a first angulation, and wherein the X-ray imaging device is configured to record a third projection image of the implant in the anatomy of the examination object in a third angulation after a forward movement of the implant along a movement axis with a tip of the implant foremost;

a system control unit configured to establish an advanced position of the tip of the implant in the third projection image;

an image system for analyzing X-ray images for image recognition;

a selecting unit configured to establish a first epipolar line for the advanced position of the tip in the first projection image by an epipolar geometry determined by way of the first angulation and the third angulation; and a display unit configured to simultaneously display the first projection image and the third projection image, wherein the first epipolar line is shown in the first projection image.

* * * * *